United States Patent
Pedain et al.

(10) Patent No.: US 6,765,111 B1
(45) Date of Patent: Jul. 20, 2004

(54) PROCESS FOR THE PRODUCTION OF POLYISOCYANATES CONTAINING ISOCYANURATE GROUPS AND THEIR USE

(75) Inventors: Josef Pedain, Cologne (DE); Manfred Bock, Sewickley, PA (US); Carl-Gerd Dieris, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1826 days.

(21) Appl. No.: 08/784,875

(22) Filed: Jan. 16, 1997

Related U.S. Application Data

(63) Continuation of application No. 08/626,308, filed on Apr. 1, 1996, which is a continuation of application No. 07/837,299, filed on Feb. 14, 1992, now abandoned, which is a continuation of application No. 07/311,920, filed on Feb. 16, 1989, now abandoned.

(30) Foreign Application Priority Data

Feb. 27, 1988 (DE) .......................................... 38 06 276

(51) Int. Cl.[7] ............................................. C08G 18/20
(52) U.S. Cl. ...................................... 560/351; 544/193
(58) Field of Search ........................... 544/193; 560/351

(56) References Cited

U.S. PATENT DOCUMENTS

| 3,487,080 A | | 12/1969 | Matsui et al. ................ 260/248 |
| 4,324,879 A | * | 4/1982 | Bock et al. |
| 4,412,073 A | | 10/1983 | Robin .......................... 544/193 |
| 4,419,513 A | | 12/1983 | Breidenbach et al. ....... 544/222 |
| 4,487,928 A | | 12/1984 | Richter et al. .............. 544/193 |
| 4,537,961 A | | 8/1985 | Robin .......................... 544/193 |
| 4,582,888 A | | 4/1986 | Kase et al. .................... 528/49 |
| 4,604,418 A | | 8/1986 | Shindo et al. .............. 524/296 |
| 4,675,401 A | | 6/1987 | Robin .......................... 544/193 |

FOREIGN PATENT DOCUMENTS

| CA | 650847 | * 10/1962 |
| DE | 3240613 | 5/1984 |
| GB | 920080 | 3/1963 |

* cited by examiner

*Primary Examiner*—Elvis O. Price
(74) *Attorney, Agent, or Firm*—Joseph C. Gil; Thomas W. Roy; Noland J. Cheung

(57) ABSTRACT

The present invention is directed to a process for the production of polyisocyanates containing isocyanurate groups by trimerizing a portion of the isocyanate groups of hexamethylene diisocyanate using N,N,N-trialkyl-N-benzyl-quaternary ammonium hydroxides as the trimerization catalyst, terminating the trimerization reaction at the desired degree of trimerization by adding a catalyst poison and/or by thermally deactivating the catalyst and removing unreacted hexamethylene diisocyanate to a residual content of at most 0.2% by weight, characterized in that a) the hexamethylene diisocyanate used as starting material is freed from carbon dioxide to a residual content of less than 20 ppm (weight) and b) the catalyst is used in a quantity of less than about 0.03% by weight, based on the weight of the hexamethylene diisocyanate used.

The present invention is also directed to the polyisocyanates containing isocyanurate groups obtained by this process and to their use, optionally blocked by blocking agents for isocyanate groups, as the isocyanate component for the production of polyisocyanate polyaddition products.

14 Claims, No Drawings

PROCESS FOR THE PRODUCTION OF POLYISOCYANATES CONTAINING ISOCYANURATE GROUPS AND THEIR USE

This application is a continuation, of application Ser. No. 08/626,308 filed Apr. 1, 1996 which is a continuation of Ser. No. 07/837,299 filed Feb. 14, 1992 (Abandoned) which is a continuation of Ser. No. 07/311,920, filed Feb. 16, 1989 (Abandoned).

BACKGROUND OF THE INVENTION

1. Field of the Invention

The present invention is directed to a new process for the production of polyisocyanates containing isocyanurate groups by trimerizing a portion of the isocyanate groups of hexamethylene diisocyanate (referred to hereinafter as "HDI"), to the products obtained by this process, and their use, optionally in blocked form, as the isocyanate component in polyisocyanate polyaddition products, preferably polyurethane lacquers.

2. Description of the Prior Art

The use of quaternary ammonium hydroxides as catalysts for the trimerization of isocyanate groups is known and has been repeatedly described. Thus, according to JP-PS 601,337 (U.S. Pat. No. 3,487,080), quaternary ammonium hydroxides are used together with certain co-catalysts. The examples primarily describe the partial trimerization of aromatic diisocyanates. However, the partial trimerization of HDI is described in the examples.

The process according to EP-A 10,589 represents a further development of the process according to the Japanese patent specification cited above. According to this prior publication, quaternary ammonium hydroxides containing hydroxyalkyl substituents are used for the trimerization of HDI. With these catalysts, HDI can be trimerized in excellent fashion without cloudiness. The disadvantage of this process is that the hydroxyalkyl ammonium hydroxides are very difficult to produce in colorless form and have to be used in relatively large quantities of up to 0.6%. Accordingly, the end products of the process, i.e. the isocyanurate polyisocyanates freed from excess starting diisocyanate, may possibly show a yellowish coloration.

EP-A 47,452 describes the production of mixed trimers based on HDI and IPDI by a process wherein starting diisocyanates which are not freed from carbon dioxide are used, necessitating comparatively large quantities of catalysts, as can be seen from the examples.

Other known processes for the production of isocyanurate polyisocyanates based on HDI are also attended by serious disadvantages. Thus, GB-PS 920,080, DE-OS 3,100,262, DE-OS 3,219,608 or DE-OS 3,240,613 for example describe processes for the trimerization of HDI using metal-containing catalysts and co-catalysts such as phenols, alcohols or tertiary amines. The metal compounds can only be removed from the end products by very elaborate processes, if at all, and can significantly affect subsequent applications and also the stability of the end products. In addition, the use of co-catalysts containing active hydrogen atoms leads to secondary reactions in which valuable isocyanate groups are consumed. The same also applies to the process according to EP-AS 155,559, wherein ammonium salts of organic acids are used as catalysts in combination with large amounts of alcoholic compounds.

In the processes according to EP-A 57,653, EP-A 89,297 and EP-A 187,105, organosilicon catalysts are used in comparatively large quantities. These compounds also cannot be completely removed from the end product and adversely affect its use.

Accordingly, an object of the present invention is to provide a new process for the partial trimerization of the isocyanate groups of HDI which combines the following advantages:

The end products are substantially colorless, i.e., have a color value (HAZEN) according to DIN 53,409 below 100.

The end products are free from cloudiness and can be dissolved without cloudiness in any of the standard lacquer solvents.

The end products contain no metal ions.

The process can be carried out using minimal quantities of catalysts without being dependent on the use of large quantities of isocyanate-reactive co-catalysts.

It has now surprisingly been found that this object can be achieved according to the present invention as described in detail hereinafter.

SUMMARY OF THE INVENTION

The present invention is directed to a process for the production of polyisocyanates containing isocyanurate groups by trimerizing a portion of the isocyanate groups of hexamethylene diisocyanate using quaternary ammonium hydroxides corresponding to the formula

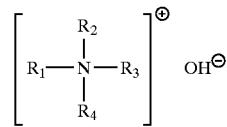

wherein $R_1$, $R_2$ and $R_3$ may be the same or different and represent alkyl radicals containing 1 to 18 carbon atoms and $R_4$ is a benzyl radical, as the trimerization catalyst, terminating the trimerization reaction at the desired degree of trimerization by adding a catalyst poison and/or by thermally deactivating the catalyst and removing unreacted hexamethylene diisocyanate to a residual content of at most 0.2% by weight, characterized in that a) the hexamethylene diisocyanate used as starting material is freed from carbon dioxide to a residual content of less than 20 ppm (weight) and b) the catalyst is used in a quantity of less than about 0.03% by weight, based on the weight of the hexamethylene diisocyanate used.

The present invention is also directed to the polyisocyanates containing isocyanurate groups obtained by this process and to their use, optionally blocked by blocking agents for isocyanate groups, as the isocyanate component for the production of polyisocyanate polyaddition products.

DETAILED DESCRIPTION OF THE INVENTION

The use of HDI which is substantially free from carbon dioxide as the starting material is crucially important to the present invention. The HDI used in accordance with the invention has a carbon dioxide content of less than 20 ppm (weight), preferably less than 10 ppm (weight) and more preferably less than 5 ppm (weight).

Technical HDI purified by distillation, which has previously been used for the production of polyisocyanates containing isocyanurate groups, contains considerable quantities (approximately 20 ppm to 100 ppm by weight) of carbon dioxide. Carbon dioxide can enter the HDI during the production process, for example during the phosgenation of carbonic acid salts of hexamethylenediamine. It can be taken up from the air during storage and can be formed by chemical reaction of the NCO groups, for example by forming carbodiimide groups or by reaction with moisture. HDI freshly purified by vacuum distillation contains, for example, 40 ppm carbon dioxide after 24 hours in a sealed container. HDI stored for a period of about 6 months can contain up to 0.6% by weight carbon-dioxide if the container is opened during the period of storage.

Carbon dioxide can be removed from HDI by blowing ultra-pure nitrogen or a noble gas, for example argon, for example at a temperature of about 0 to 70° C., through HDI. Although it is possible to apply a higher temperature, this does not afford any significant advantages. Carbon dioxide may also be removed by distillation in a stream of nitrogen or noble gas. The method by which the carbon dioxide is removed is not crucial to the process according to the invention. However, substantially complete removal of carbon dioxide is generally not possible merely by distillation.

The catalysts used in the process according to the invention are quaternary ammonium hydroxides corresponding to the formula

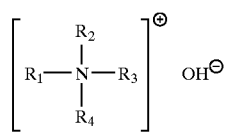

wherein $R_1$, $R_2$ and $R_3$ may be the same or different and represent alkyl radicals containing 1 to 18 carbon atoms, preferably 1 to 4 carbon atoms, more preferably methyl groups and $R_4$ is a benzyl radical.

A particularly preferred catalyst is N,N,N-trimethyl-N-benzyl-ammonium hydroxide.

The quaternary ammonium hydroxides to be used in accordance with the invention and their production are known. They are commercially available either in the form of colorless substances or solutions or as already stated, only as brightly colored solutions. This natural color of the catalysts is often a disadvantage in the processes corresponding to the prior art cited above for the production of isocyanurate polyisocyanates based on HDI, because in these known processes the catalysts have to be used in comparatively large quantities. By contrast, in the process according to the invention, the natural color of the catalysts is not an important factor because the catalyst is only used in extremely low concentrations.

In the process according to the invention, the catalyst is used in a positive amount of less than 0.031% by weight, preferably in a positive amount of less than 0.01% by weight and bore preferably in a quantity of from 0.0005 to 0.005% by weight, based on the HDI used. The particular optimal quantity of catalyst depends on the type of quaternary ammonium compound used and may readily be determined by a preliminary test. When N,N,N-trimethyl-N-benzyl-ammonium hydroxide is used, it is sufficient to use particularly small quantities.

In contrast to the process according to JP-PS 601,337, co-catalysts, especially isocyanate-reactive co-catalysts, are not necessary and may be omitted in the process according to the invention. In particular, there is no need to use relatively large quantities of compounds containing isocyanate-reactive groups such as phenols, oximes and, in particular, methanol. Secondary reactions between a portion of the isocyanate groups of HDI and the isocyanate-reactive groups are avoided. Valuable isocyanate groups are not consumed and the formation of cloudiness attributable to these secondary products may be prevented.

Accordingly, the trimerization process according to the invention may also be carried out very effectively when no urethane groups are formed during the catalysis process. However, since many of the catalysts used in the process according to the invention are dissolved in solvents containing hydroxyl groups or themselves carry hydroxy groups, the formation of urethane groups in the process according to the invention is not ruled out. It is particularly preferred to use solvents which do not contain any isocyanate-reactive groups for the catalysts. The catalyst may also be used in solvent-free form.

When hydroxyl group-containing solvents are used, it is preferred to use those which do not form solid reaction products with HDI at room temperature and which reduce the functionality of the end products as little as possible. Hydroxyl group-containing solvents such as these include 2-ethylhexane-1,3-diol and 2-ethylhexanol. Examples of suitable solvents with no isocyanate-reactive groups include dimethylformamide, dimethylacetamide, dimethylsulfoxide and acetonitrile.

Due to the extremely small quantities of catalyst, dosing and incorporation of the pure, undiluted catalyst, although possible, is not easy, particularly when the process is carried out continuously on an industrial scale. Accordingly, it is preferred to use heavily diluted catalyst solutions. Concentrations below 5% by weight, preferably below 1% by weight are particularly suitable. To prepare catalyst solutions such as these, it is often advisable to remove solvents present in the catalysts such as methanol by mild distillation after the addition of a suitable solvent of the type mentioned by way of the example above.

The trimerization reaction is preferably carried out in the absence of a solvent (apart from the solvent for the catalyst), although this does not rule out the use of standard lacquer solvents during the trimerization reaction. Examples include esters such as butyl acetate or ethoxyethylacetate; ketones such as methylisobutylketone or methylethylketone; hydrocarbons such as xylene; and mixtures of such solvents. However, since unreacted HDI is removed after the trimerization reaction, the use of such solvents during the trimerization reaction results in unnecessary additional expense.

To carry out the trimerization reaction, the catalyst is added to HDI which has been substantially freed from carbon dioxide. The catalyst may be added in increments during the trimerization reaction. The trimerization reaction is generally carried out at a temperature of about 0 to 100° C., preferably about 20 to 80° C. and is terminated at a degree of trimerization of about 10 to 40%, preferably about 20 to 30%. By "degree of trimerization" is meant the percentage of isocyanate groups present in the starting diisocyanate which react during the trimerization reaction.

To terminate the trimerization reaction, a suitable catalyst poison is generally added to the reaction mixture. Suitable catalyst poisons include inorganic acids such as hydrochloric acid, phosphorous acid or phosphoric acid; sulfonic acids or derivatives thereof such as methanesulfonic acid, p-toluenesulfonic acid or p-toluenesulfonic acid methyl or ethyl ester; and perfluorinated sulfonic acids such as nonafluoro-butanesulfonic acid. Particularly suitable deactivators, i.e. catalyst poisons, include acidic esters of phosphorous acid or phosphoric acid such as dibutyl phosphite, dibutylphosphate or di-(2-ethylhexyl)-phosphate, which are preferably used in the form of a dilute solution in HDI. The deactivators are generally added to the reaction mixture in a quantity at least equivalent to the catalyst. However, since the catalysts can partly decompose during the trimerization reaction, the addition of a sub-equivalent quantity of the deactivator is often sufficient. On the other hand, to guarantee safe termination of the reaction, it is often also advisable to use a larger than equivalent quantity, for example twice the equivalent quantity of deactivator. Accordingly, it is preferred to use deactivators (catalyst poisons) in up to twice the equivalent quantity, based on the quantity of catalyst used. When thermally labile catalysts are used, it is often unnecessary to add a catalyst poison. When these catalysts are used, it is often sufficient to terminate the reaction by brief heating of the reaction mixture to temperatures above 100° C. (thermal decomposition, i.e. deactivation of the catalyst).

After deactivation, excess HDI is removed in a suitable manner such as extraction (for example using n-hexane as extractant) or, preferably, thin-layer distillation in a vacuum, to a residual HDI content of at most 0.2% by weight, preferably less than 0.1% by weight.

The end products of the process according to the invention are colorless liquids having a color value (HAZEN) according to DIN 53,409 below 100, preferably below 50, an isocyanate content of about 10 to 24% by weight and a viscosity at 23° C. of about 500 to 10,000 mPa.s.

Since only very small quantities of catalyst are used in the process according to the invention, the quantity of deactivator, i.e. the catalyst poison, can also be kept correspondingly small, with the result that the end products of the process according to the invention contain only very small quantities of secondary products formed from catalyst and catalyst poison which remain in solution and do not affect the subsequent use of the products. Even when the process is carried out using HDI, which has not been purified beforehand in the usual way by distillation to remove traces of chlorine-containing compounds via weakly basic compounds such as metal oxides or sodium hydrogen carbonate, clear and colorless end products are obtained. By virtue of their low viscosity, the end products of the process according to the invention are suitable for the production of polyisocyanate polyaddition products by reaction with compounds containing at least two isocyanate-reactive groups and are particularly suitable for the production of solventless or low-solvent two-component polyurethane lacquers.

When the end products of the process according to the invention are used in accordance with the invention, they may be blocked by blocking agents for isocyanate groups. Suitable blocking agents include the compounds mentioned by way of example in EP-A 10,589, page 15, lines 14 to 26 (U.S. Pat. No. 4,324,879, previously incorporated by reference).

The end products of the process according to the invention are used for the production of high-quality two-component polyurethane lacquers, preferably in combination with known polyhydroxy polyesters, polyhydroxy polyethers and, in particular, polyhydroxy polyacrylates. In addition to the relatively high molecular weight polyhydroxyl compounds mentioned, the lacquers may also contain low molecular weight, preferably aliphatic polyols. Combinations of the end products of the process according to the invention with polyhydroxyl polyacrylates represent particularly valuable two-component binders for high-quality car repair lacquers which have outstanding weather resistance.

Polyamines, particularly in blocked form as polyketimines or oxazolidines, may also be used as reactants for the end products of the process according to the invention. The quantitative ratios in which the optionally blocked polyisocyanates according to the invention and the isocyanate-reactive compounds mentioned are reacted in the production of polyisocyanate polyaddition products lacquers are selected such that for every (optionally blocked) isocyanate group, there are about 0.8 to 3, preferably about 0.9 to 1.8 hydroxyl, amino and/or carboxyl groups.

To accelerate the hardening process, it is possible to use the known catalysts from isocyanate chemistry, for example tertiary amines such as triethylamine, pyridine, methyl pyridine, benzyldimethylamine, N,N-dimethylaminocyclohexane, N-methyl piperidine, pentamethyl diethylenetriamine, N,N'-endo-ethylene piperazine or N,N'-dimethyl piperazine; and metal salts such as iron(III) chloride, zinc chloride, zinc(II) ethylcaproate, tin(II)-2-ethylcaproate, dibutyltin(IV) dilaurate or molybdenum glycolate.

In blocked form the products according to the invention in combination with polyhydroxyl compounds are used in particular for the production of stoving lacquers which can be hardened at temperatures of about 80 to 180° C. (depending on the blocking agent used) to form high-quality lacquer coatings.

To prepare ready-to-use lacquers the optionally blocked polyisocyanate, the polyfunctional reactant, optionally an isocyanate polyaddition catalyst and known additives (such as pigments, dyes, fillers and levelling agents) are thoroughly mixed with one another and homogenized in a standard mixing unit, such as a sand mill, either with or without solvents and diluents.

The paints and coating compositions may be applied to the article to be coated either in solution, from the melt or in solid form by standard methods such as spread coating, roll coating, casting, spray coating, fluidized bed coating or electrostatic powder spraying.

The lacquers containing the polyisocyanates according to the invention produce films which adhere surprisingly well to metal substrates and which are particularly resistant to light, color stable under heat and highly abrasion-resistant. In addition, they are distinguished by extreme hardness, elasticity, high resistance to chemicals, high gloss, excellent weather resistance and good pigmentability.

In the following examples, percentages are percentages by weight unless otherwise indicated.

EXAMPLES

Example 1

Preparation of Catalyst Solution I 600 g 2-ethylhexane-1,3-diol were added to and stirred with 1000 g of a commercial, colorless 40% solution of N,N,N-trimethyl-N-benzylanimonium hydroxide in methanol. The methanol was then removed with thorough stirring in a water jet pump vacuum at 30 to 40° C. The 40% stock solution was adjusted with additional 2-ethylhexane-1,3-diol to a catalyst concentration of about 0.5%.

Example 2

Preparation of Catalyst Solution II

The procedure was as in Example 1, except that dimethylformamide was used instead of 2-ethylhexane-1,3-diol to replace methanol and for further dilution. A 0.5% catalyst solution in dimethylformamide was obtained.

Example 3

Preparation of Comparison Catalyst solution III 60 g 2-ethylhexanol were added to 100 g of a 70% solution in methanol of N,N,N-trimethyl-N-(2-hydroxypropyl)-ammonium hydroxide (prepared by the reaction of trimethylamine with propylene oxide in methanol) and the methanol was subsequently removed in a water jet pump vacuum. The solution was then adjusted with additional 2-ethylhexanol to a catalyst concentration of 4%. The solution was brown in color.

Example 4

According to the Invention

In a stirred reactor 3200 g HDI were degassed for about 10 minutes at about 20° C. by applying a vacuum (50 mbar) and stirring vigorously. The gas space of the apparatus was then filled with pure nitrogen. A stream of pure, dry nitrogen was then vigorously passed through the liquid for about 1 hour at around 25° C. Prior to treatment the HDI had a $CO_2$ content of 44 ppm; the $CO_2$ content was reduced to 2 ppm after the described treatment. More nitrogen was passed through the reaction mixture for the remainder of the reaction.

32 g (0.96 mmol of base) of catalyst solution (I) were then added dropwise over a period of 15 to 30 minutes, followed by heating for 30 minutes to 60° C. Since the reaction was now slightly exothermic, the contents of the reactor were kept at 60 to 65° C. by cooling. The reaction abated after about 0.5 h, at which time the NCO content of the crude product measured 42%. The crude product was then stirred for about 1 h at 60° C. until an NCO content of 38% was reached. The reaction was then terminated by the addition of 0.32 g of a 25% solution of dibutylphosphate (0.38 mmol) in HDI, followed by stirring for 15 minutes. The liquid was then allowed to cool to ambient temperature and excess HDI was removed by thin-layer distillation.

1382 g of a clear, light polyisocyanate characterized by the following data were obtained:

Viscosity: 1800 mPa.s/23° C.

Color value (HAZEN) according to DIN 53,409: 20

NCO content: 22.3%

Free HDI content: 0.05%

Dilutability with xylene: was diluted without cloudiness to below a solids content of 10%

Example 5

Comparison Example

The procedure was as in Example 4. 3200 g HDI were introduced into an apparatus which was then degassed by applying a vacuum and filled with nitrogen. Thereafter, however, no nitrogen, was blown through, so that as a result nitrogen was not introduced into the liquid but only passed over. The $CO_2$ content of the HDI was only negligibly reduced by this measure to 38 ppm.

32 g of catalyst solution (I) were then added as described in Example 1, followed by heating to 60° C. No reaction was observed and there was hardly any reduction in the NCO content. An additional 32 g of catalyst solution were added after 4 h at 60° C.; the reaction still did not start. After an additional 64 g of catalyst was added, a reaction began and was terminated at an NCO content of 38.2% by the addition of 1.58 g of a 25% solution of dibutylphosphate. After cooling to 25° C, the solution was in the form of a cloudy liquid which gradually precipitated a white deposit. After removal of free HDI by thin-layer distillation, a cloudy yellow product having an NCO content of 21.4% was obtained. The clouding did not disappear after dilution with butyl acetate. Dilution with xylene intensified the clouding. The product was unsuitable for use in high-quality PUR lacquers.

Example 6

According to the Invention

In a stirred reactor, 798 g of freshly distilled hexamethylene diisocyanate were vigorously stirred in a vacuum (50 mbar) for 30 minutes at 20° C. The gas space of the apparatus was then filled with highly pure nitrogen. The carbon dioxide content of the HDI was 44 ppm. A stream of pure, dry nitrogen was then vigorously passed through the liquid for 1 hour at 30 to 40° C. Re-determination of the $CO_2$ revealed a content of 2 ppm.

Throughout the reaction, dry nitrogen was passed through the reaction mixture. To initiate the trimerization reaction, 12 g catalyst solution II were added dropwise over a period of about 30 minutes, followed by slow heating to 70° C. The reaction was exothermic and was sustained for 1 hour at about 75° C. without any further supply of heat. Another 12 g of catalyst solution were then added. The reaction mixture was then left to react for another 30 minutes with thorough stirring. The reaction was terminated at an NCO content of 42.4% by the addition of 0.6 g (equivalent ratio of catalyst to terminator=approx. 1:1) of a 25% solution of dibutylphosphate in HDI. After 15 minutes, the reaction mixture was subjected to thin-layer distillation at 130° C. to separate solvent and HDI. 230 g of a polyisocyanate characterized by the following data were obtained:

Viscosity: 2200 mPa.s/23° C.

NCO content: 22.0%

Free HDI content: 0.09%

Color value: 30 (DIN 53,409)

Example 7

According to the Invention

The procedure was as in Example 6. The reaction was terminated at an NCO content of 38.0%. After termination of the reaction and after thin-layer distillation at 120° C., 350 g of a product having, the following characteristic data were obtained:

Viscosity: 3000 mPa.s/23° C.

NCO content: 21.7%

Color value: 40 (DIN 53,409)

Free HDI content: 0.1%

Example 8–10

Comparison Examples

Example 11–12

According to the Invention

The procedure was as described in Example 1, i.e. $CO_2$ was removed from the HDI with a vigorous stream of nitrogen at 40 to 50° C. The other conditions of the polymerization reaction are shown in Table 1. The catalyst was deactivated with dibutylphosphate with one exception (Example 10). Table 1 also sets forth the NCO content of the reaction mixture at which termination of the polymerization reaction was initiated. Table 2 sets forth the characteristic data of the end product after removal of excess HDI.

TABLE 1

| EXAMPLE | HDI (g) | $CO_2$ CONTENT AFTER $N_2$ TREATMENT | CATALYST SOLUTION OF EXAMPLE 3 | CATALYST SOLUTION OF EXAMPLE 1 | DEACTIVATION BY HEATING OR WITH DIBUTYLPHOSPHATE (25% SOLUTION IN HDI) | NCO CONTENT OF THE CRUDE SOLUTION |
|---|---|---|---|---|---|---|
| 8 (Comp) | 3000 | 4 ppm | 12.4 g | — | 2 g at 50° C. | 39.2% |
| 9 (Comp) | 3000 | 6 ppm | 12.4 g | — | 0.5 g at 60° C. | 34.5% |
| 10 (Comp) | 2500 | 2 ppm | 7 g | — | by heating to 120° C. | 41.3% |
| 11 | 2500 | 2 ppm | — | 11.9 g | 0.13 g at 60° C. | 42.0% |
| 12 | 2500 | 10 ppm | — | 20 g | 0.52 at 70° C. | 38.1% |

TABLE 2

| EXAMPLE | QUANTITY OF PRODUCT AFTER REMOVAL OF HDI | NCO CONTENT | VISCOSITY 23° C./mPa.s | COLOR VALUE (HAZEN), DIN 53,409 | FREE HDI CONTENT |
|---|---|---|---|---|---|
| 8 (Comp) | 1296 g | 22.8% | 1700 | 70 | 0.12% |
| 9 (Comp) | 560 g | 20.2% | 9800 | 90 | 0.09% |
| 10 (Comp) | 880 g | 23.2% | 1800 | 70 | 0.05% |
| 11 | 805 g | 23.7% | 1500 | 30 | 0.05% |
| 12 | 1200 g | 22.0% | 2100 | 40 | 0.05% |

Although the invention has been described in detail in the foregoing for the purpose of illustration, it is to be understood that such detail is solely for that purpose and that variations can be-made therein by those skilled in the art without departing from the spirit and scope of the invention except as it may be limited by the claims.

What is claimed is:

1. A process for the preparation of a polyisocyanate containing isocyanurate groups which comprises
    a) trimerizing a portion of the isocyanate groups of hexamethylene diisocyanate, which contains less than 10 ppm by weight of carbon dioxide, in the presence of a positive amount of less than 0.03% by weight, based on the weight of hexamethylene diisocyanate, of a quaternary ammonium hydroxide catalyst corresponding to the formula

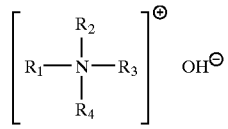

wherein
    $R_1$, $R_2$ and $R_3$ may be the same or different and represent alkyl radicals containing 1 to 18 carbon atoms and
    $R_4$ is a benzyl radical,
    b) terminating the trimerization reaction at the desired degree of trimerization by the addition of a catalyst poison and/or by thermal deactivation and
    c) subsequently removing unreacted hexamethylene diisocyanate such that said polyisocyanate contains at most 0.2% by weight of hexamethylene diisocyanate, based on the weight of said polyisocyanate.

2. The process of claim 1 wherein said catalyst is used in a positive amount of less than 0.01% by weight, based on the weight of hexamethylene diisocyanate.

3. The process of claim 1 wherein said catalyst comprises N,N,N-trimethyl-N-benzyl-ammonium hydroxide.

4. The process of claim 2 wherein said catalyst comprises N,N,N-trimethyl-N-benzyl-ammonium hydroxide.

5. The process of claim 1 which comprises terminating the trimerization reaction by adding a catalyst poison comprising dibutyl phosphate.

6. The process of claim 1 which comprises terminating the trimerization reaction by adding a catalyst poison comprising di-(2-ethylhexyl)-phosphate.

7. A polyisocyanate containing isocyanurate groups which is prepared by a process comprising
    a) trimerizing a portion of the isocyanate groups of hexamethylene diisocyanate, which contains less than 10 ppm by weight of carbon dioxide, in the presence of a positive amount of less than 0.03% by weight, based on the weight of hexamethylene diisocyanate, of a quaternary ammonium hydroxide catalyst corresponding to the formula

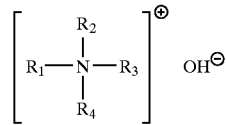

wherein
    $R_1$, $R_2$ and $R_3$ may be the same or different and represent alkyl radicals containing 1 to 18 carbon atoms and
    $R_4$ is a benzyl radical,
    b) terminating the trimerization reaction at the desired degree of trimerization by the addition of a catalyst poison and/or by thermal deactivation and
    c) subsequently removing unreacted hexamethylene diisocyanate such that said polyisocyanate contains at most 0.2% by weight of hexamethylene diisocyanate, based on the weight of said polyisocyanate.

8. The polyisocyanate of claim 7 wherein said catalyst is used in a positive amount of less than 0.01% by weight, based on the weight of hexamethylene diisocyanate.

9. The polyisocyanate of claim 7 wherein said catalyst comprises N,N,N-trimethyl-N-benzyl-ammonium hydroxide.

10. The polyisocyanate of claim 8 wherein said catalyst comprises N,N,N-trimethyl-N-benzyl-ammonium hydroxide.

11. The polyisocyanate of claim 7 which comprises terminating the trimerization reaction by adding a catalyst poison comprising dibutyl phosphate.

12. The polyisocyanate of claim 7 which comprises terminating the trimerization reaction by adding a catalyst poison comprising di-(2-ethylhexyl)-phosphate.

13. A process for the preparation of a polyisocyanate polyaddition product which comprises a) preparing a polyisocyanate based on hexamethylene diisocyanate and containing isocyanurate groups in accordance with the process of claim 1 and b) reacting the product of step (a) with a compound containing at least two isocyanate-reactive groups.

14. The process of claim 13 wherein said polyisocyanate polyaddition product is a polyurethane and said compound containing at least two isocyanate-reactive groups comprises a polyol.

* * * * *